(12) United States Patent
Derrick et al.

(10) Patent No.: US 6,452,041 B1
(45) Date of Patent: Sep. 17, 2002

(54) OLEFINATION PROCESS TO ITACONATE AND SUCCINATE DERIVATIVES

(75) Inventors: Andrew Michael Derrick; Nicholas Murray Thomson, both of County of Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/977,822

(22) Filed: Oct. 15, 2001

Related U.S. Application Data
(60) Provisional application No. 60/253,434, filed on Nov. 28, 2000.

(30) Foreign Application Priority Data

Oct. 16, 2000 (GB) ................................................ 0025310

(51) Int. Cl.[7] .......................... C07C 67/30; C07C 69/74; C07C 63/64; C07C 53/134; C07C 35/00
(52) U.S. Cl. ....................... 560/211; 562/495; 562/496; 562/599; 560/76; 560/127
(58) Field of Search ................................ 562/495, 496, 562/599; 560/76, 127, 211

(56) References Cited

U.S. PATENT DOCUMENTS
4,939,288 A 7/1990 Talley .......................... 560/81

FOREIGN PATENT DOCUMENTS
| EP | 0561758 | 9/1993 |
| EP | 0673911 | 9/1995 |
| WO | WO 9504033 | 2/1995 |
| WO | WO 9802445 | 1/1998 |
| WO | WO 9931041 | 6/1999 |
| WO | WO 9935124 | 7/1999 |
| WO | WO 0027855 | 5/2000 |
| WO | WO 0147901 | 7/2001 |

OTHER PUBLICATIONS

Owton, et al.; Tert–Butyl 3–carboxyethyl–3–phosphonodiethylpropionate A Novel Reagent for Stobbe–Like Condensations; *Synthetic Communications*; 23(15), 2119–2125 (1993).

Fray, et al.; Discovery of Potent and Selective Succinyl Hydroxamate Inhibitors of Matrix Metalloprotease–3 (Stromelysin–1); *Bioorganic & Medicinal Chemistry Letters*; 11:571–574 (2001).

*Primary Examiner*—Paul J. Killos
*Assistant Examiner*—Zachary Tucker
(74) *Attorney, Agent, or Firm*—Peter C. Richardson; Paul H. Ginsburg; Adrian G. Looney

(57) ABSTRACT

An efficient and selective process, capable of scale-up, to make itaconate derivatives of formula (IV), and/or succinate derivatives of formula (V) and/or (VI) by asymmetric hydrogenation of the itaconate derivatives.

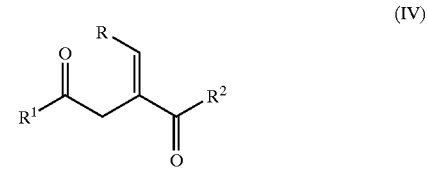

(IV)

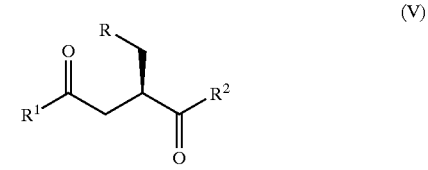

(V)

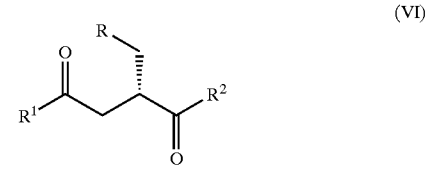

(VI)

wherein R, $R^1$ and $R^2$ are as defined herein.

23 Claims, No Drawings

OLEFINATION PROCESS TO ITACONATE AND SUCCINATE DERIVATIVES

The application claims the benefit of U.S. Provisional Patent Application No. 60/253,434, filed Nov. 28, 2000 and U.K. Patent Application No. 0025310.4, filed Oct. 16, 2000, both of which are hereby incorporated by reference in their entirety.

The invention described herein relates to a novel olefination process which is useful for making certain itaconate and succinate derivatives.

It is desirable in a number of instances to be able to have an efficient and selective process, capable of scale-up, to make itaconate derivatives of formula (I), and/or succinate derivatives of formula (II) and/or (III):

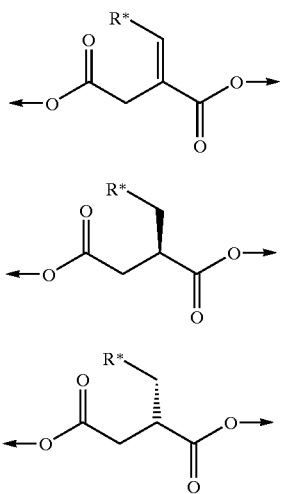

wherein "R*" is a sterically bulky group.

Of particular interest to us is the provision of compounds of the formula (IV), (V) and (VI), especially (IV) and (V);

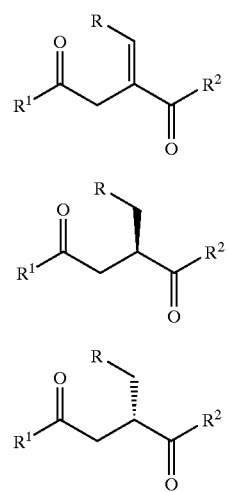

wherein R is aryl, $C_{3-8}$ cycloalkyl, $C_{1-10}$ alkyl, (aryl)$C_{1-10}$ alkylene, ($C_{3-8}$ cycloalkyl)$C_{1-10}$ alkylene, heterocyclyl, (heterocyclyl)$C_{1-10}$ alkylene, (aryl)$C_{3-8}$ cycloalkylene, ($C_{3-8}$ cycloalkyl)arylene or ($C_{1-10}$ alkylaryl)$C_{1-10}$ alkylene, wherein "aryl" is a mono- or bicyclic partially or fully unsaturated carbocyclic ring system containing from 4 to 10 atoms, such as phenyl or naphthyl, or a partially or fully unsaturated mono- or bicyclic heterocyclic moiety having up to 10 atoms in the ring system and with up to 4 hetero-atoms in the said ring system each independently selected from N, O and S, said carbocyclic ring system and heterocyclic moiety being optionally substituted by one or more substituents each independently selected from halogen, $NO_2$, $NH_2$, $CO_2R^9$, phenyl, $C_{1-6}$ alkyl(optionally substituted by one or more halogen), and $C_{1-6}$ alkoxy(optionally substituted by one or more halogen), and "heterocyclyl" is a 3- to 8-membered mono or bicyclic saturated heterocyclic group having from 1 to 4 ring hetero-atoms each independently selected from N, O and S, optionally substituted by one or more substituents each independently selected from halogen, $NO_2$, $NH_2$, $CO_2R^9$, phenyl, $C_{1-6}$ alkyl(optionally substituted by one or more halogen), and $C_{1-6}$ alkoxy(optionally substituted by one or more halogen);

$R^1$ is $C_{1-6}$ alkoxy, $R^2$ is OH or $O^-M^+$;

$R^9$ is H or $C_{1-6}$ alkyl; and $M^+$ is the cation of a metal such as sodium, lithium or potassium, or is a protonated amine moiety such as (mono-, di- or tri-$C_{1-10}$ alkyl) ammonium, (mono-, di- or tri-$C_{3-10}$ cycloalkyl) ammonium, ($C_{1-10}$ alkyl)$_{n1}$ ($C_{3-10}$ cycloalkyl)$_{n2}$ammonium, anilinium, benzylammonium, triethanolammonium, or (S)-α-methylbenzylammonium, where n1 and n2 are each independently selected from 1 or 2 with the proviso that the sum of n1 and n2 is not greater than 3;

Alkyl groups, and groups containing alkyl moieties such as alkoxy and alkylene groups, can be straight chain or branched if the number of carbon atoms allows, Halogen means fluorine, chlorine or bromine, Cycloalkyl groups attached to an ammonium moiety can contain 1, 2, or 3 rings, where the number of carbon atoms allows, for example adamantanammonium.

Production of compounds related to (IV), (V) and (VI) has been disclosed previously, e.g. by Owton et al, in Synthetic Communications, 23(15), 2119–2125 (1993), M J Burk et al, Angew. Chem. Int. Edn. (Eng.) (1998) 37, 13/14, 1931–1933, Monsanto, U.S. Pat. No. 4,939,288, and by Chirotech Technology Ltd. in International Patent Application publication no. WO 99/31041. Known olefination reactions leading to systems related to (IV), generally result in poor E/Z selectivity, (for a review of the Stobbe condensation, see Org.React. 1951, 6, 1–73). Where selectivity has been controlled, however, for example by the use of phosphorus reagents, the substitution pattern is different from that required by us in formula (IV)(e.g. Monsanto, Owten, supra).

The products of the Owten chemistry are exemplified by compounds of the formula (VII):

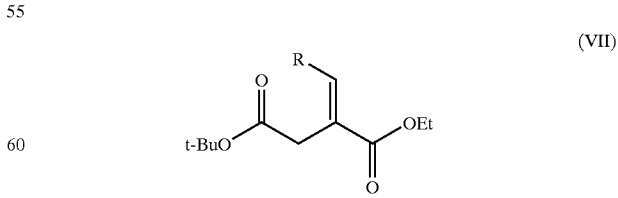

on which we attempted hydrolysis of the ethyl ester using conventional chemistry. In our hands this resulted in scrambling of the olefinic moiety resulting overall in a mixture of stereoisomers and regioisomers.

Use of the Monsanto chemistry gives products of the formula (VIII):

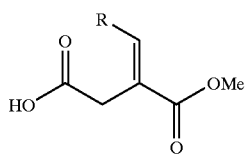

(VIII)

which has the wrong substitution pattern for our requirements.

We have discovered a new and efficient olefination method which can be used to make compounds of formula (IV) in good yield and with good trans-selectivity, and which products can then be asymmetrically reduced to give compounds of formula (V) and (VI). The olefination is base-catalysed and can be used with enolisable aldehydes or aldehyde derivatives without significant amounts of self-condensation products. We also surprisingly observe no substantial double bond migration to give deconjugated isomers of (IV) under the basic conditions, which would afford other geometric and regio-isomers, which is another significant problem with similar prior art olefinations.

Our olefination system is thus particularly useful when highly selective production of the compounds (IV), (V) and/or (VI) is required, or where separation of (IV), (V) and/or (VI) and/or the respective isomers thereof, may be difficult or undesirable, such as in processing to make pharmaceutical products and regulatory starting materials for such products.

Thus, according to the present invention, there is provided a process for the preparation of compounds of formula (IV) as defined above, comprising reaction of an aldehyde of formula RCHO, or a protected derivative thereof such as a hemiacetal or adduct thereof such as a bisulphite, wherein R is as defined above, with a phosphorus compound of formula (IX):

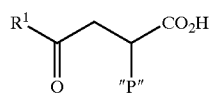

(IX)

or a metal carboxylate salt thereof such as a sodium, lithium or potassium carboxylate salt thereof, wherein $R^1$ is as defined above, and "P" is a phosphonate moiety of formula —P(O)(OR$^3$)(OR$^4$), wherein $R^3$ and $R^4$ are either each independently selected from H, $C_{1-6}$ alkyl, benzyl and phenyl (optionally substituted by one or more $C_{1-6}$ alkyl), or $R^3$ and $R^4$ taken together are $C_{2-5}$ alkylene, or "P" is a phosphorane moiety of formula —(PR$^5$R$^6$R$^7$)$^+$ X$^-$ wherein $R^5$, $R^6$ and $R^7$ are each independently selected from $C_{1-6}$ alkyl and phenyl, and X is bromine, chlorine or iodine, in the presence of a sodium, lithium or potassium $C_1$–$C_6$ alkoxide base, in an inert solvent, and at a temperature of from –80° C. to 20° C.

Preferably the reaction time is less than 24 hours.

Preferably R is (aryl)$C_{1-10}$ alkylene or ($C_{3-8}$ cycloalkyl) $C_{1-10}$ alkylene.

More preferably R is phenylethyl, cyclohexylethyl or (2-methyl-1,1'-biphenyl-4-yl)ethyl.

Preferably $R^1$ is t-butoxy.

Preferably $R^2$ is OH, O$^-$Li$^+$, O$^-$Na$^+$, O$^-$K$^+$, O$^-$cyclohexylammonium$^+$, O$^-$adamantanammonium$^+$, O$^-$triethanolammonium$^+$ or O$^-$(S)-α-methylbenzylammonium$^+$.

Preferably the olefination reaction is carried out using the aldehyde RCHO or the sodium bisulphite adduct thereof RCH(OH)SO$_3^-$Na$^+$.

Preferably "P" is P(O)(OC$_2$H$_5$)$_2$, P(O)(OCH$_2$CH$_2$O) or a triphenylphosphinium halide moiety.

More preferably P is P(O)(OC$_2$H$_5$)$_2$.

Preferably the base is potassium t-butoxide, sodium t-butoxide or sodium methoxide.

When the base alkoxide and $R^1$ are different there is a possibility of transesterification taking place during the olefination reaction. We have found that this apparently has no detrimental effect on the course of the reaction at the olefination centre, in terms of stereochemistry, and may not be important with respect to the use made of the product, e.g. if it is used as an intermediate and the $R^1$ moiety is later removed, e.g. by displacement, hydrolysis or deprotection.

Preferably the olefination reaction solvent is anhydrous tetrahydrofuran, anhydrous toluene or $R^1$H, where $R^1$ takes the meaning as specified above with respect to the compounds of formulae (IV), (V) and (VI), or a mixture thereof.

More preferably the reaction solvent is selected from tetrahydrofuran and toluene when the aldehyde RCHO is used as a substrate, and selected from tetrahydrofuran/t-butanol and toluene when the bisulphite adduct is used as substrate.

Preferably the reaction is carried out at a temperature from –20° C. to 10° C.

More preferably the reaction is carried out at a temperature from –10° C. to 10° C.

Most preferably the reaction is carried out at a temperature from 0° C. to 5° C.

When the aldehyde RCHO is used as substrate, it is preferable to add the phosphorus compound to the base/solvent mixture, followed by addition of the aldehyde. Alternatively, the phosphorus compound and aldehyde are combined, then the base is added. A further alternative is to add the base to the phosphorus compound followed by addition of the aldehyde.

When the bisulphite is used as the substrate, it is preferable to add the base to a mixture of the bisulphite adduct and the phosphorus compound, or, alternatively, the bisulphite is added to a mixture of the phosphorus compound and the base. 'Bisulphite' or 'bisulphite adduct' is taken to mean an α-hydroxysulphonate, which is the product of the reaction of an aldehyde with sodium, potassium or lithium bisulphite. Other suitable bisulphites are known in the art.

The skilled person will appreciate that the substrates, and starting material of formula (IX), can be obtained from commercial sources, or made by methods known in the art, e.g. by adaptation of the methods herein described in the sections below, and/or adaptation thereof, for example by methods known in the art. Suitable guides to synthesis, functional group transformations, use of protecting groups, etc. are found in standard organic chemistry textbooks, for example, "Comprehensive Organic Transformations" by R C Larock, VCH Publishers Inc. (1989), "Advanced Organic Chemistry" by J March, Wiley Interscience (1985), "Designing Organic Synthesis" by S Warren, Wiley Interscience (1978), "Organic Synthesis—The Disconnection Approach" by S Warren, Wiley Interscience (1982), "Guidebook to Organic Synthesis" by R K Mackie and D M Smith, Longman (1982), "Protective Groups in Organic Synthesis" by T W Greene and P G M Wuts, John Wiley and Sons Inc. (1999), and P J Kocienski, in "Protecting Groups", Georg Thieme Verlag (1994), and any updated versions of said standard works.

The above olefination process is optionally followed by conversion of the product of formula (IV) where $R^2$ is $O^-M^+$ wherein $M^+$ is a metal such as Na, Li or K, to a compound of formula (IV) where $R^2$ is OH by treatment with a proton source, which may optionally be converted to a compound of formula (IV) wherein $R^2$ is $O^-M^+$ (where $M^+$ is a protonated amine moiety as previously defined), by treatment with a corresponding amine.

A further aspect of the invention is the asymmetric hydrogenation of itaconate compounds of the formula (IV) to give succinate compounds of the formula (V) or (VI).

Asymmetric hydrogenation of compounds of formula (IV) may be achieved in a multitude of ways, including methods known in the art. For example use may be made of catalytic hydrogenation using chiral rhodium or ruthenium complex of an optically active biphosphine or biphosphinite compound such as (4R,5R)-(−)-O-Isopropylidene-2,3-dihydroxy-1,4-bis(diphenylphosphino)butane [(R,R)-DIOP], (R,R)-(−)-1,2-Bis[(O-methoxyphenyl)(phenyl)phosphino]ethane [(R,R)-DIPAMP], (−)-(R)—N,N-Dimethyl-1-((S)-1',2-Bis(Diphenylphosphino)ferrocenyl)ethylamine [(R)-(S)-BPPFA], (−)-(2S,4S)-2-Diphenylphosphinomethyl-4-diphenylphosphino-1-t-butoxycarbonylpyrrolidine [(S,S)-BPPM], (2S,3S)-(−)-Bis(diphenylphosphino)butane [(S,S)-CHIRAPHOS], R-(+)-1,2-Bis(diphenylphosphino)propane [(R)-PROPHOS], (2R,3R)-(−)-2,3-Bis(diphenylphosphino)bicyclo[2.2.1]hept-5-ene [(R,R)-NORPHOS], (R)-(+)-2,2'-Bis(diphenylphosphino)-1,1'-binaphthyl [(R)-BINAP], (R)-1,2-bis(diphenylphosphino)-1-cyclohexylethane [(R)-CYCPHOS], (2R,4R)-(+)-2,4-Bis(diphenylphosphino)pentane [(R,R)-BDPP], N-benzyl-(3R,4R)-3,4-bis(diphenylphosphino)pyrrolidine [(R,R)-DEGPHOS], (−)-1,2-Bis((2R,5R)-2,5-dimethylphospholano)benzene [(R,R)-Me-DUPHOS], (−)-1,2-Bis((2R,5R)-2,5-diethylphospholano)benzene [(R,R)-Et-DUPHOS], N,N'-bis[(R)-(+)-α-methylbenzyl]-N,N'-bis(diphenylphosphino)ethylenediamine [(R)-PNNP], (R)-(−)-2,2'-bis(dicyclohexylphosphino)-6,6'-dimethyl-1,1'-biphenyl [(R)-BICHEP], (1 R,2S,4R,5S)-2,5-dimethyl-7-phosphadicyclo[2.2.1]heptane[(R,S,R,S)-Me-PENNPHOS], (2S,2'S)-Bis(diphenylphosphino)-(1S,1'S)-bicyclopentane [(S,S)-BICP], 1,1'-bis[(2S,4S)-2,4-diethylphosphetano]ferrocene [(S,S)-Et-FerroTANE], (R,R)-1,2-bis(di-t-butylmethylphosphino)methane [(R,R)-t-butyl-minPHOS], (R)-(+)-2,2'-Bis(di-p-tolylphosphino)-1,1'-binaphthyl [(R)-tol-BINAP], (R)-(+)-2-(Diphenylphosphino)-2'-methoxy-1,1'-binaphthyl [(R)-MOP], (R)-(+)-1-(2-Diphenylphosphino-1-naphthyl)isoquinoline [(R)-QUINAP], Methyl α-D-glucopyranoside-2,6-dibenzoate-3,4-di(bis(3,5-dimethylphenyl)phosphinite) (CARBOPHOS), (R)-(−)-1-[(S)-2-(Diphenylphosphino)ferrocenyl]ethyldicyclohexylphosphine [(R)-(S)-JOSIPHOS], (R)-(−)-4,12-Bis(diphenylphosphino)-[2.2]-paracyclophane [(R)-PHANEPHOS], (R)-(6,6'-Dimethoxybiphenyl-2,2-diyl)-bis(diphenylphosphine) [(R)-MeO-BIPHEP], ], (R)-(6-Chloro-6'-methoxybiphenyl-2,2-diyl)-bis(diphenylphosphine) [(R)-Cl-MeO-BIPHEP] or 2,2'-bis(diphenylphosphino)-4,4',6,6'-tetrakis(trifluoromethyl)-1,1'-biphenyl (BIFUP) which are well-known to the skilled chemist working in the asymmetric hydrogenation art.

It is to be appreciated that other examples include related structures, such as those with alternative alkyl substituents, and stereoisomers of the above-mentioned examples.

Some catalysts are mentioned in the Examples, and other suitable catalysts which may be useful are mentioned in the following publications and references therein, all of which are herein incorporated by reference in their entirety:

U.S. Pat. No. 4,939,288 (Monsanto);

International Patent Application publication no. WO 98/02445 (Chiroscience Ltd);

International Patent Application publication no. WO 99/31041 (Chirotech Technology Ltd);

European Patent Application 0 673 911 A1 (Takasago International Corporation);

International Patent Application publication no. WO 00/27855 (Chiroscience Technology Ltd);

X. Zhang, Enantiomer (1999), 4(6), 541;

H. Tye, J C S Perkin I, (2000) (3) 275–298;

J. M. Brown, Compr. Asymmetric Catal. I–III (1999), 1, 121–182;

M. J. Burk, Spec.Chem. (1998) 18(2) 58–59, 62;

T. Yamagishi, Organomet. News (1995) (4), 113–118;

J. P. Genet, ACS Symp. Ser. (1996) 641 (Reductions in Organic Synthesis), 31–51;

H. Kumobayashi, Recl.Trav.Chim.Pays-Bas (1996) 115 (4) 201–210;

M. J. Burk et al, Pure Appl. Chem. (1996) 68(1) 37–44;

H. Takaya et al, Catal. Asymm.Synth. (1993) 1–39;

S. Akutagawa, Chirality Ind. (1992) 325–339; A. Borner et al, Transition Met.Org.Synth. (1998) 2 3–13;

D. G. Blackmond, CATTECH (1998) 2(1), 17–32;

R. Noyori, Acc.Chem.Res. (1997) 30(2) 97–102;

W. S. Knowles, Chem.Ind.(Dekker) (1996) 68(Catalysis of Organic Reactions) 141–152;

U. Behrens, Spec.Chem.(1996) 16(5) 174, 176–177;

R. Noyori, Acta Chem.Scand. (1996) 50(4), 380–390;

H. B. Kagan, Mec., Phys., Chim., Astron., (1996) 322(2) 131–143;

A. S. C. Chan et al, Chem.Ind.(Dekker) (1994) 53(Catalysis of Organic Reactions) 49–68;

K. Inoguchi et al, Synlett (1992) (3) 169–78;

G. Webb et al, Catal.Today (1992) 12(2–3) 319–337;

D. Arntz et al; Catal.Met.Complexes (1991) 12(Met.Promoted Sel.Org.Synth.) 161–189;

K. Harada, Asymmetric Synth. (1985) 5 345–383; and

W. S. Knowles, Acc. Chem.Res.(1983) 16(3) 106–112.

The person skilled in the art will appreciate that the use of one enantiomer of such chiral catalysts will give one enantiomer (V) or (VI), and use of the other enantiomer will give the other enantiomer.

Some of the suitable catalysts may be generically defined by the formula P*-cat-P** wherein "cat" is a metal such as rhodium or ruthenium, and P* and P** each independently represents a chiral phosphine moiety, optionally conjoined.

Preferably the catalyst used for reduction of compounds of formula (IV) where $R^2$ is $O^-M^+$, is ruthenium based, such as ruthenium complexes of BINAP and derivatives thereof, such as [(S)-2,2'-bis(diphenylphosphino-1,1'-binaphthyl]chloro(p-cymene)ruthenium chloride.

Preferably the catalyst used for reduction of compounds of formula (IV) where $R^2$ is OH, is rhodium-based, such as Rh-DUPHOS (1,2-bis[(2S,5S)-2,5-diethylphospholano]benzene-(1,5-cyclooctadien)-rhodium (I) tetrafluoroborate) or Rh-Ferrotane (1,1'-bis[(2S,4S)-2,4-diethylphosphetano]ferrocene-(1,5-cyclooctadiene)-rhodium (I) tetrafluoroborate).

Suitably the hydrogenation of the acid (IV, $R^2$ is OH), can be carried out in the presence of a base such as sodium bicarbonate, cyclohexylamine, isopropylamine, t-butylamine, adamantanamine, or (S)-(α-methylbenzylamine. The hydrogenation can be carried out on a preformed salt (IV, $R^2$ is $O^-M^+$).

The reaction is suitably carried out in an inert solvent such as an aqueous $C_{1-3}$ alcohol e.g. aqueous methanol, or $C_{1-3}$ alcohol e.g. methanol. Other suitable inert solvents include, but is not limited to, tetrahydrofuran, ethyl acetate, tert-butyl methyl ether, α, α, α-trifluorotoluene, methylene chloride or toluene. The reaction is carried out optionally at an elevated temperature, under a positive pressure of hydrogen.

Suitable temperatures for good yield and selectivity for the ruthenium-catalysed hydrogenation has been found to be approximately 60° C., and for the rhodium-catalysed reactions at approximately 20° C.

The skilled chemist will realise that suitable conditions for particular hydrogenations of compounds of formula (IV) can be found by routine modification of those mentioned herein.

A further aspect of the invention are novel compounds of formula (IV), (V) and (VI), and novel processes, including those mentioned in the Examples.

The invention is illustrated in the following Examples and Preparations section, but is not limited to these illustrations.

Preparation 1

3-(diethoxyphosphoryl)succinic Acid 1-tert-butyl Ester

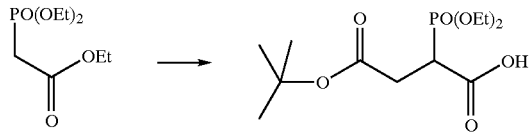

Triethylphosphonoacetate (12.0 Kg, 53.5 mol) was added over 30 minutes to a stirred solution of potassium tert-butoxide (7.20 Kg, 64.2 mol) in THF (118 liters), between 0 and 5° C., under nitrogen. The mixture was warmed to 25–30° C. where it was stirred for 1 hour and then added over 45 minutes to a solution of tert-butyl bromoacetate (11.5 Kg, 59.0 mol) in THF (28 liters), between 0 and 5° C., under nitrogen. The mixture was stirred at 0–5° C. for 1 hour and then demineralised water (6.1 liters) and ethanol (30 liters) were added. A solution of potassium hydroxide (4.2 Kg, 75.0 mol) in demineralised water (84 liters) was then added over 2 hours, between –5 and 0C. The mixture was stirred at –10° C. for 16 hours and then a solution of citric acid (16.5 Kg, 85.8 mol) in demineralised water (32 liters) was added. The mixture was concentrated in vacuo to a volume of 180 liters and then ethyl acetate (90 liters) was added. The organic phase was separated and the aqueous phase was re-extracted with ethyl acetate (30 liters). The combined organic phases were washed with water (30 liters) and then stripped and replaced with cyclohexane by distillation at atmospheric pressure, at a constant volume of 72 liters. tert-Butylmethyl ether (18 liters) was added and the mixture was stirred at 20–25° C. for 12 hours and then filtered. The residue was washed with a mixture of cyclohexane (16 liters) and tert-butylmethyl ether (3.6 liters) then dried in vacuo for 16 hours to give the title compound as a colourless solid (10.0 Kg, 60% yield, 98% pure by HPLC).

$^1$H-NMR (CDCl$_3$) δ5: 4.20–4.10 (4H, m), 3.49–3.36 (1H, m), 300–2.85 (1H, m), 2.72–2.60 (1 H, m), 1.20 (9H, s), 1.37–1.27 (6H, m)

EXAMPLE 1

(E)-2-[2-(tert-butoxy)-2-oxoethyl]-5-phenyl-2-pentenoic Acid

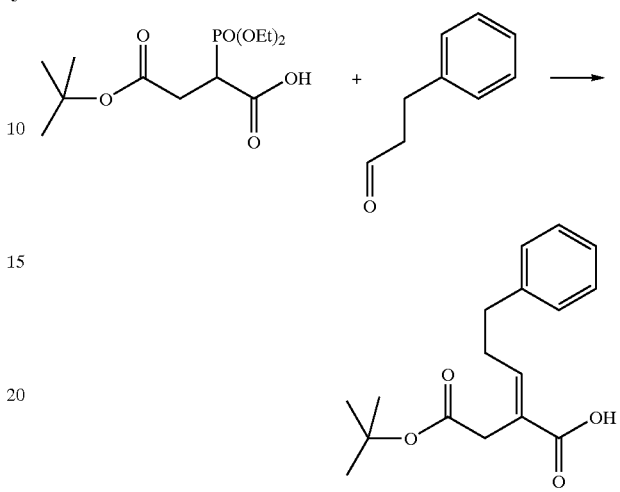

A solution of 3-(diethoxyphosphoryl)succinic acid 1-tert-butyl ester (100 g, 0.32 mol) in THF (300 ml) was added dropwise over 15 min to a stirred solution of potassium tert-butoxide (110 g, 0.98 mol) in THF (300 ml), between –10 and –5° C., under nitrogen. The mixture was stirred at –10° C. for 15 min and then a solution of hydrocinnamaldehyde (46.8 g, 0.35 mmol) in THF (100 ml) was added dropwise over 15 min, between –13 and –8° C. The mixture was stirred at –10° C. for 30 min and then a solution of citric acid (111 g, 0.58 mol) in demineralised water (500 ml), and ethyl acetate (500 ml), were added. The pH was adjusted to pH 4 with aqueous sodium hydroxide solution (50%) and the phases were separated. The aqueous fraction was washed with ethyl acetate (500 ml) and the combined organic fractions were washed with saturated sodium bicarbonate solution (500 ml), citric acid solution (10%, 500 ml) and demineralised water (500 ml) and then concentrated in vacuo. The resulting solid was slurried in cyclohexane (470 ml) for 1 hour and then the mixture was filtered. The residue was washed with cyclohexane (2×50 ml) and dried in vacuo to leave the title compound as a colourless solid (76 g, 81% yield, 99% pure by HPLC).

MS: 289 [(M-H)]hu –

$^1$H-NMR (CDCl$_3$) δ: 7.33–7.16 (5H, m), 7.05 (1H, br t), 3.20 (2H, s), 2.89 (2H, br, t), 2.50 (2H, br dd), 1.41 (9H, s)

EXAMPLE 2

(R)-2-[2-(tert-butoxy)-2-oxoethyl]-5-phenylpentanoic Acid

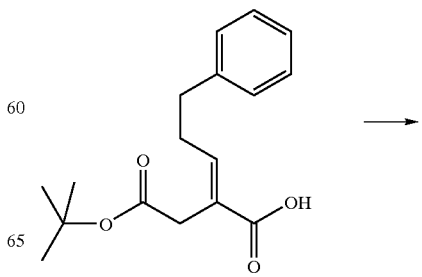

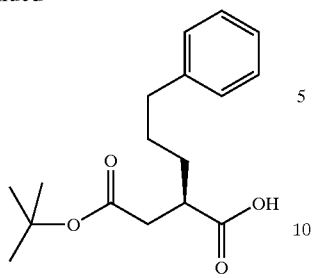

A solution of (E)-2-[2-(tert-butoxy)-2-oxoethyl]-5-phenyl-2-pentenoic acid (5.8g, 20 mmol) and 1,1'-bis[(2S,4S)-2,4-diethylphosphetano]ferrocene-(1,5-cyclooctadiene)-rhodium (I) tetrafluoroborate (7.4 mg, 10 μmol) in methanol (10 ml) was stirred at 20–25° C. for 24 hours, under hydrogen (4 atmospheres, 60 p.s.i.). The mixture was then concentrated in vacuo to leave the title compound as a yellow oil (5.8 g, 98% conversion, enantiomeric excess= 97%, 95% pure by NMR).

$^1$H-NMR (CDCl$_3$) δ: 7.30–7.17 (5H, m), 2.85–2.78 (1H, m), 2.66–2.58 (3H, m), 2.37 (1 H, br dd), 1.75–1.51 (4H, m), 1.40 (9H, s)

EXAMPLE 3

(R)-2-[2-(tert-butoxy)-2-oxoethyl]-5-phenylpentanoic Acid cyclohexylamine Salt

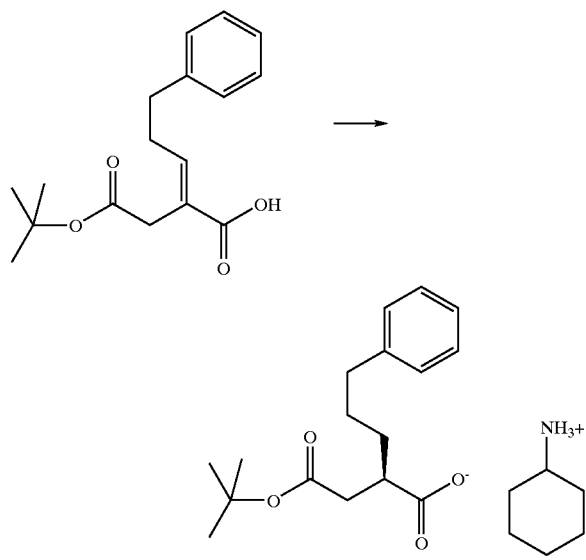

A stirred solution of cyclohexylamine (266 ml, 2.32 mol), (E)-2-[2-(tert-butoxy)-2-oxoethyl]-5-phenyl-2-pentenoic acid (688 g, 2.37 mol) and [(S)-2,2'-bis(diphenylphosphino-1,1'-binaphthyl]chloro(p-cymene)ruthenium chloride (4.4g, 4.7 mmol) in methanol (6.9 liters) was heated to 60° C., under hydrogen (60 p.s.i.), for 47 hours and then allowed to cool to 20–25° C. (enantiomeric excess=88%). The mixture was filtered through a filter aid Celite® and then the solvent was stripped and replaced with acetone by distillation at atmospheric pressure, at a constant volume of 4.2 liters. The resulting suspension was cooled to 20–25° C., stirred for 4 hours and then filtered. The residue was washed with acetone (2×1 liter) and then dried in vacuo at 45° C. for 16 hours to leave the title compound as a colourless solid (590 g, 64% yield, enantiomeric excess=98.9%, 97% pure by HPLC).

$^1$H-NMR (CD$_3$OD) δ: 7.23–7.09 (5H, m), 3.05–2.98 (1H, m), 2.64–2.56 (3H, m), 2.53 (1H, dd, J 15.2, 7.2 Hz), 2.23 (1H, dd, J 15.2, 7.2 Hz), 2.00–1.97, (2H, m), 1.85–1.81 (2H, m), 1.72–1.20 (10H, m), 1.40 (9H, s)

EXAMPLE 4

(R)-2-[2-(tert-butoxy)-2-oxoethyl]-5-phenylpentanoic Acid Sodium Salt

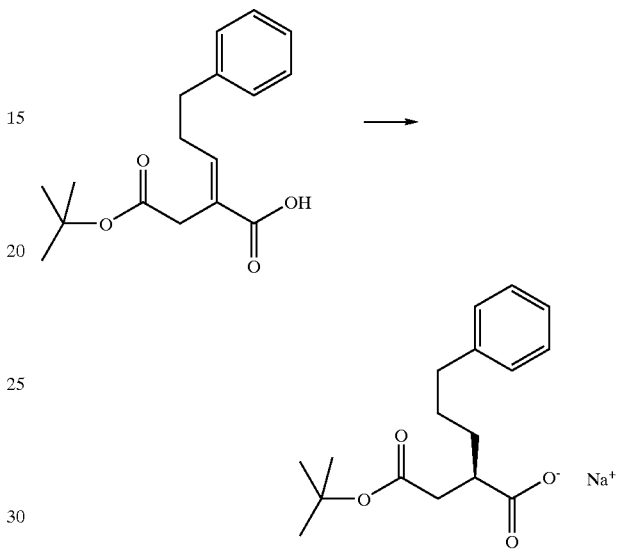

A stirred solution of sodium bicarbonate (28.6 g, 0.34 mol), (E)-2-[2-(tert-butoxy)-2-oxoethyl]-5-phenyl-2-pentenoic acid (100 g, 0.34 mol) and [(S)-2,2'-bis(diphenylphosphino-1,1'-binaphthyl]chloro(p-cymene)ruthenium chloride (0.63 g, 0.68 mmol) in methanol (750 ml) and water (250 ml) was heated to 60° C., under hydrogen (60 p.s.i.), for 24 hours and then allowed to cool to 20–25° C. (enantiomeric excess 87%). The mixture was filtered through a filter aid Celite® and the solvent was stripped and replaced with acetonitrile by distillation at atmospheric pressure, at a constant volume of 500 ml. The resulting suspension was cooled to 20–25° C. and was stirred for 24 hours, then filtered. The residue was washed with acetonitrile (3×25 ml) and then dried in vacuo at 45° C. for 3 hours to leave the title compound as a colourless solid (65 g, 61% yield, enantiomeric excess= 94.3%, 95% pure by NMR).

$^1$H-NMR (CD$_3$OD) δ: 7.23–7.10 (5H, m), 2.62–2.58 (3H, dd, J 15.2, 7.6 Hz), 2.22 (1 H, dd, J 15.2, 7.6 Hz), 1.74–1.42 (4H, m), 1.40 (9H, s)

EXAMPLE 5

(E)-2-[2-(tert-butoxy)-2-oxoethyl]-5-cyclohexyl-2-pentenoic Acid Cyclohexylamine Salt

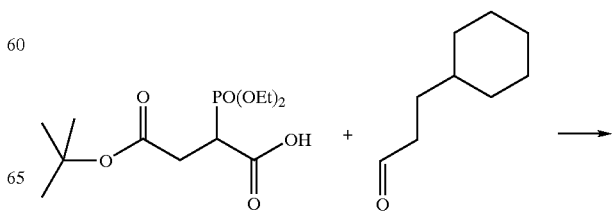

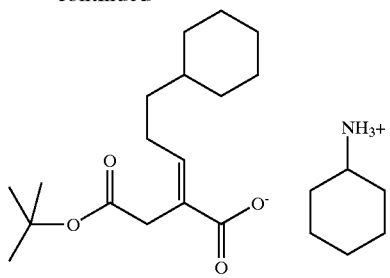

Potassium tert-butoxide (20.2 g, 0.18 mol) was added portionwise over 10 minutes to a solution of 3-(diethoxyphosphoryl)succinic acid 1-tert-butyl ester (25.4 g, 82- mmol) in THF (115 ml), at 0° C., under nitrogen. The mixture was stirred at 0° C. for 40 minutes and then cooled to −20° C. A solution of 3-cyclohexylpropan-1 -al (11.5 g, 82 mmol in THF (60 ml) was added dropwise over 10 minutes between −20 and −10° C., under nitrogen. The mixture was stirred between −20 and −5° C. for 3 hours and then aqueous citric acid (10%, 250 ml) and ethyl acetate (200 ml) was added. The organic phase was separated and the aqueous fraction was washed with ethyl acetate (200 ml). The combined organic fractions were washed with saturated sodium bicarbonate solution (2×100 ml), aqueous citric acid solution (10%, 100 ml) and demineralised water (100 ml) and then concentrated in vacuo. The resulting solid was taken up in ethyl acetate (150 ml) and cyclohexylamine (9.4 ml, 82 mmol) was added dropwise over 5 minutes at 20–25° C. The mixture was stirred at 20–25° C. for 16 hours and then filtered. The residue was dried in vacuo at 40° C. for 4 hours to leave the title compound as a colourless solid (21.7 g, 67% yield, 95% pure by NMR).

¹H-NMR (CD₃OD) δ: 6.70 (1H, t, J 7.2 Hz), 3.26 (2H, s), 3.10–3.00 (1H, m), 276–2.63 (2H, m), 2.19–0.90 (23H, m), 1.41 (9H, s)

EXAMPLE 6

(R)-2-[2-(tert-butoxy)-2-oxoethyl]-5-cyclohexylpentanoic Acid

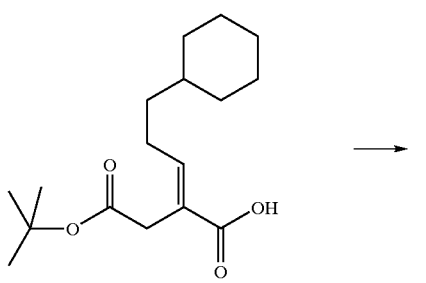

A solution of (E)-2-[2-(tert-butoxy)-2-oxoethyl]-5-cyclohexyl-2-pentenoic acid (0.74 g, 2.5 mmol) and 1,1'-bis [(2S,4S)-2,4-diethylphosphetano]ferrocene-(1,5-cyclooctadiene)-rhodium (I) tetrafluoroborate (18 mg, 25 μmmol) in methanol (2.5 ml) was stirred at 20–25° C. for 24 hours, under hydrogen (4 atmospheres, 60 p.s.i.). The mixture was then concentrated in vacuo to leave the title compound as a yellow oil (0.74 g, 98% conversion, enantiomeric excess=95%, 95% pure by NMR).

¹H-NMR (CDCl₃) δ:: 2.82–2.76 (1H, m), 2.60 (1H, br dd), 2.37 (1H, br dd), 1.70–1.60 (6H, m), 1.51–1.30 (3H, m), 1.42 (9H, s), 1.23–1.11 (6H, m), 0.96–0.80 (2H, m)

EXAMPLE 7

(R)-2-[2-(tert-butoxy)-2-oxoethyl]-5-cyclohexylpentanoic Acid

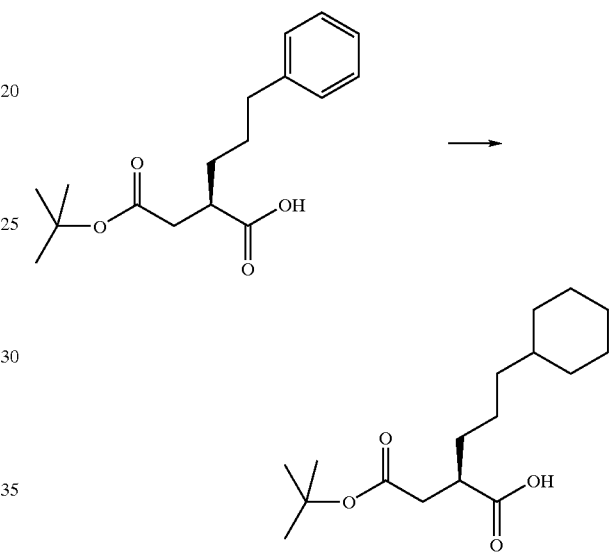

A solution of (R)-2-[2-(tert-butoxy)-2-oxoethyl]-5-phenylpentanoic acid (2.2 g, 7.5 mmol) and 5% rhodium on carbon (0.22 g) in methanol (220 ml) was stirred at 20–25° C., under hydrogen (10 atmospheres, 150 p.s.i.) for 24 hours and then filtered through celite. The filtrate was concentrated in vacuo to leave the title compound as an oil (2.0 g, 89% yield, 95% pure by NMR).

¹H-NMR (CDCl₃) δ: 2.82–2.76 (1H, m), 2.60 (1H, br dd), 2.37 (1H, br dd), 1.70–1.60 (6H, m), 1.51–1.30 (3H, m), 1.42 (9H, s), 1.23–1.11 (6H, m), 0.96–0.80 (2H, m)

EXAMPLE 8

(R)-2-[2-(tert-butoxy)-2-oxoethyl]-5-cyclohexylpentanoic Acid Cyclohexylamine Salt

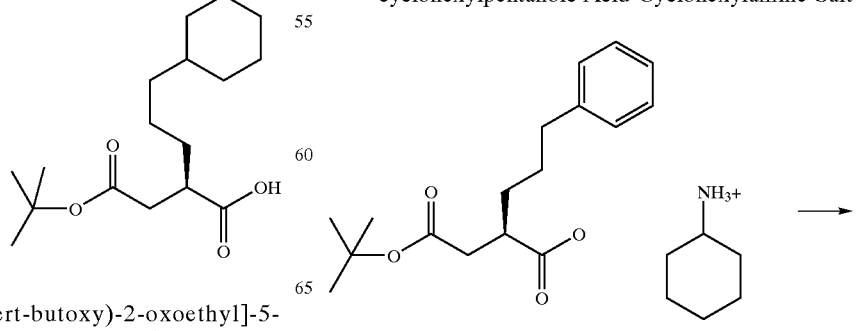

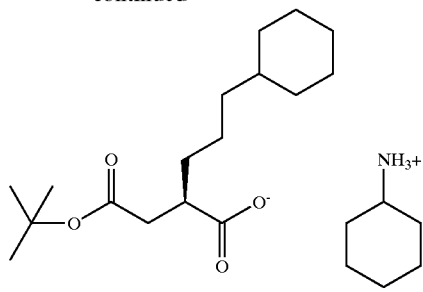

(R)-2-[2-(tert-Butoxy)-2-oxoethyl]-5-phenylpentanoic acid cyclohexylamine salt (691 g, 1.77 mol) and ethyl acetate (7.0 liters) were added to an aqueous solution of citric acid (10%, 6.3 liters) and the organic phase was separated, washed with water (7.0 liters) and concentrated in vacuo to a yellow oil. A solution of the oil and 5% rhodium on carbon (51.6 g) in methanol (7.0 liters) was stirred at 20–25° C., under hydrogen (10 atmospheres, 150 p.s.i.) for 48 hours and then filtered through celite. To the filtrate was added cyclohexylamine (202 ml, 1.77 mol) and the methanol solution was stripped and replaced with methylethyl ketone by distillation at atmospheric pressure, to a volume of 5.5 liters. The mixture was allowed to cool to 20–25° C. where it was stirred for 48 hours and then filtered. The residue was washed with methylethyl ketone (2×500 ml) and then dried in vacuo at 45° C. for 4 hours to leave the title compound as a colourless solid (495 g, 71% yield, 99% pure by HPLC).

$^1$H-NMR (CD$_3$OD) δ: 3.06–2.99 (1H, m), 2.63–2.56 (1H, m), 2.53 (1H, dd, J 15.2, 7.2 Hz), 2.23 (1H, dd, J 15.2, 7.2 Hz), 2.02–1.97 (2H, m), 1.77–1.15 (21H, m), 1.43 (9H, s), 0.93–0.82 (2H, m)

EXAMPLE 9

(R)-2-[2-(tert-butoxy)-2-oxoethyl]-5-cyclohexylpentanoic Acid Sodium Salt

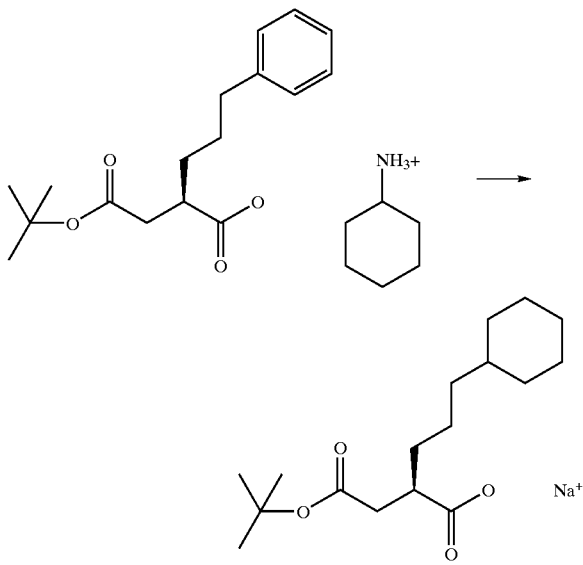

(R)-2-[2-(tert-Butoxy)-2-oxoethyl]-5-phenylpentanoic acid cyclohexylamine salt (6.8 g, 17 mmol) and ethyl acetate (100 ml) were added to an aqueous solution of citric acid (10%, 100ml) and the organic phase was separated and washed with water (100 ml). Iso-propyl alcohol (20 ml) and 5% rhodium on alumina (51.6 g) were added and the mixture was stirred at 20–25° C., under hydrogen (10 atmospheres, 150 p.s.i.) for 48 hours and then filtered through celite. To the filtrate was added a solution of sodium hydroxide (0.67 g, 17 mmol) in water and the mixture was stripped and replaced with acetonitrile by distillation at atmospheric pressure to a volume of 30 ml. The mixture was allowed to cool to 20–25° C. and was stirred for 24 hours. The mixture was cooled to 0° C. and then filtered. The residue was washed with acetonitrile (2×10 ml) and then dried in vacuo at 45° C. for 2 hours to leave the title compound as a colourless solid (3.8 g, 69% yield, 95% pure by NMR).

$^1$H-NMR (CD$_3$OD) δ: 2.62–2.57 (1H, m), 2.53 (1H, dd, J 14.8, 7.2 Hz), 2.23 (1H, dd, J 14.8, 7.2 Hz), 1.76–1.18 (15H, m), 1.44 (9H, s), 0.93–0.82 (2H, m)

Preparation 2

Sodium 1-hydroxy-3-(2-methyl-1,1'-biphenyl-4-yl)-1-propanesulfonate

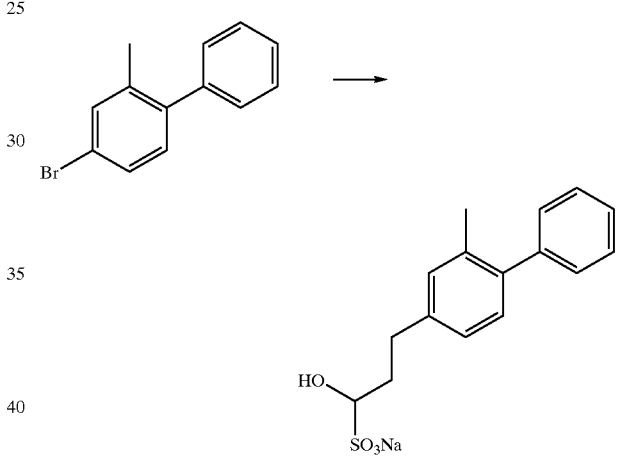

A stirred solution of 4-bromo-2-methyl-1,1'-biphenyl (20 g, 81 mmol), allyl alcohol (14 ml, 0.20 mol), tetrabutylammonium chloride (22 g, 81 mmol), sodium bicarbonate (17 g, 0.20 mol), palladium(II)acetate (0.91 g, 4.0 mmol) and tri-o-tolylphosphine (2.5 g, 8.1 mmol) in acetonitrile (200 ml) was heated to reflux for 1 hour, under nitrogen, and then cooled. Ethyl acetate (200 ml) was added and the mixture was washed with water (2×200 ml), aqueous citric acid solution (10%, 100 ml) and brine (100 ml). Magnesium sulphate (20g) and charcoal (2 g) were added and the mixture was filtered and concentrated in vacuo to an oil. The oil was taken up in methanol (100 ml) and a solution of sodium metabisulfite (11.2 g) in water (20 ml) was added dropwise, over 10 min. The resulting mixture was stirred at 20–25° C. for 16 hours and then filtered. The residue was washed with ethyl acetate (3×20 ml) and dried in vacuo to leave the title compound as a solid (15.9 g, 42% yield, 95% pure by NMR).

$^1$H-NMR (DMSO) δ: 7.49–7.30 (5H, m), 7.11–7.04 (3H, m), 5.26 (1 H, br d), 3.84–3.78 (1H, m), 2.81–2.70 (1H, m), 2.20 (3H, s), 2.12–1.99 (1H, m), 1.85–1.74 (1H, m)

EXAMPLE 10

(E)-2-[2-(tert-butoxy)-2-oxoethyl]-5-(2-methyl-1,1'-biphenyl-4-yl)-2-pentenoic Acid Cyclohexylamine Salt

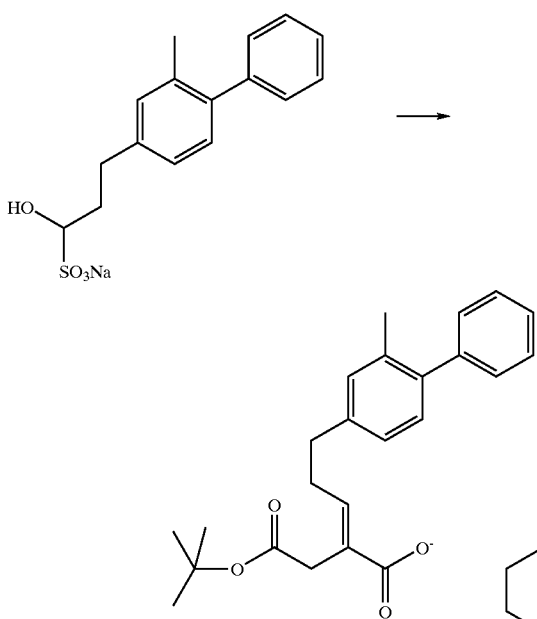

A solution of potassium tert-butoxide (6.6 Kg, 59 mol) in THF (22 liters) was added over 1 hour to a stirred solution of sodium 1-hydroxy-3-(2-methyl-1,1'-biphenyl-4-yl)-1-propanesulfonate (4.55 Kg, 13.8 mol) and 3-(diethoxyphosphoryl)succinic acid 1-tert-butyl ester (4.94 Kg, 15.9 mol) in THF (5.2 liters) and tert-butanol (18.3 liters), from −5 to 0° C., under nitrogen. The mixture was stirred from −5 to 0° C. for 4 hours and then a solution of citric acid (12.0 Kg, 62 mol) in demineralised water (28 liters) was added in one portion. The pH was adjusted to pH4–5 by the addition of aqueous sodium hydroxide solution (40%) and the organic phase was separated. The organic phase was concentrated in vacuo to a volume of approximately 25 liters and then recombined with the aqueous phase. Ethyl acetate (28 liters) was added and the organic phase was separated and then washed with a solution of sodium bicarbonate (3.18 Kg) in demineralised water (45 liters). Demineralised water (15 liters) was added and the pH was adjusted to pH 4–5 by the addition of a solution of citric acid (2.27 Kg) in demineralised water (23 liters). The organic phase was separated, washed with demineralised water (14 liters) and then azeotropically dried by distillation at atmospheric pressure at a constant volume of 56 liters. The reaction was cooled to 35 to 40° C. and cyclohexylamine (1.10 Kg, 11.1 mol) was added in one portion. The mixture was cooled to 20–25° C. and was stirred for 18 hours. The mixture was then cooled to 0° C., and was stirred for 2 hours and then filtered. The residue was washed with ethyl acetate (5 liters), then dried in vacuo at 40–45° C. to leave the title compound as a colourless solid (4.1 Kg, 61% yield, 89% pure by HPLC).

$^1$H-NMR (CDCl$_3$) δ: 7.42–7.30 (5H, m), 7.16 (1H, d, J 7.6 Hz), 7.15–7.05 (2H, m), 6.83 (1 H, t, J 7.2 Hz), 3.29 (2H, s), 2.50–2.43 (2H, m), 2.26 3H, s), 2.03–1.98 (2H, m), 1.78–1.71 (2H, m), 1.61–1.57 (1H, m), 1.44 (9H, s), 1.30–1.10 (5H, m)

EXAMPLE 11

(E)-2-[2-(tert-butoxy)-2-oxoethyl]-5-(2-methyl-1,1'-biphenyl-4-yl)-2-pentenoic Acid Adamantanamine Salt A solution of potassium phosphate tribasic (160 g, 0.762 moles) in demineralised water (500 ml) was added over 15 minutes to a stirred slurry of sodium 1-hydroxy-3-(2-methyl-1,1'-biphenyl-4-yl)-1-propanesulfonate (125 g, 0.381 moles) in toluene (1500 ml) and demineralised water (1000 ml). The mixture was stirred at 20–25° C. for 16 hours. The organic phase was separated and the aqueous phase was extracted with toluene (100 ml). The combined organic extracts were washed with demineralised water (1000 ml), and the solution was azeotropically dried by distillation of toluene at 40° C. under reduced pressure. The volume of solution was reduced to 250 ml, and allowed to cool to 20–25° C. Meanwhile, 3-(diethoxyphosphoryl) succinic acid 1-tert-butyl ester (112 g, 0.360 moles) was added portionwise over 10 minutes to a solution of sodium tert-butoxide (114 g, 1.175 moles) in toluene (1120 ml) at −10° C. under nitrogen. The mixture was stirred for 30 minutes at −10° C. The toluene solution prepared previously was added over 45 minutes between −10° C. and 0° C. The mixture was stirred at −10° C. for 1 hour and aqueous citric acid solution (10% w/v, 1000 ml) was added. The biphasic mixture was stirred at 20–25° C. for 16 hours. The organic phase was separated and washed with demineralised water (1000 ml) . The organic phase was azeotropically dried by distillation at 40° C. under reduced pressure at a constant volume of 1330 ml. The solution was maintained at 40–45° C., and a solution of adamantanamine (53 g, 0.350 moles) in toluene (665 ml) was added in one portion. The mixture was cooled to 20–25° C., and was stirred for 16 hours. The precipitate was collected by filtration, washed with toluene (150 ml) and dried in vacuo at 50° C. to leave the title compound as a colourless solid (153 g, 76% yield).

$^1$H-NMR (CDCl$_3$) δ: 7.42–7.05 (8H, m), 6.91 (1 H, t, J 7.2 Hz), 3.29 (2H, s), 2.79–2.71 (2H, m), 2.52–2.43 (2H, m), 2.25 (3H, s),2.08 (3H, s), 1.81 (6H s), 1.65 (6H s), 142 (9H,s).

EXAMPLE 12

(E)-2-[2-(tert-butoxy)-2-oxoethyl]-5-(2-methyl-1 1'-biphenyl-4-y )-2-pentenoic Acid Sodium Salt

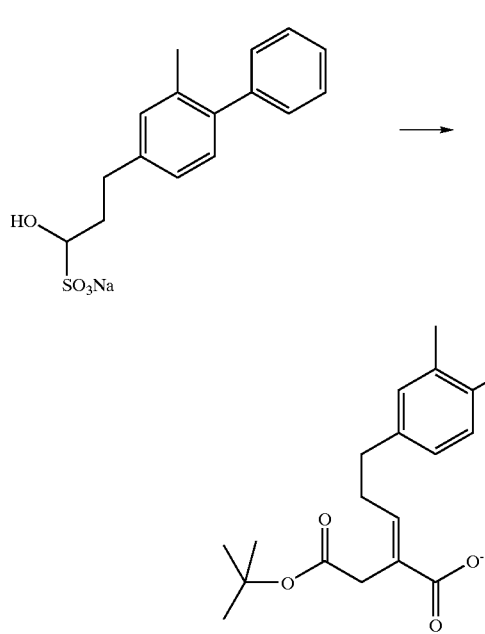

A solution of potassium tert-butoxide (7.25 g, 64.6 mmol) in THF (24 ml) was added over 1 hour to a stirred solution of sodium 1-hydroxy-3-(2-methyl-1,1'-biphenyl-4-yl)-1-propanesulfonate (5.0 g, 15.2 mmol) and 3-(diethoxyphosphoryl)succinic acid 1-tert-butyl ester (5.5 g, 17.7 mmol) in THF (6 ml) and tert-butanol (30 ml), between −5 and 0° C., under nitrogen. The mixture was stirred between −5 and 0° C. for 4 hours and then a solution of citric acid (13.2 g) in demineralised water (132 ml) was added in one portion. The pH was adjusted to pH4–5 by the addition of aqueous sodium hydroxide solution (40%) and the organic phase was separated. The organic phase was concentrated in vacuo and then recombined with the aqueous phase. Ethyl acetate (55 ml) was added and the organic phase was separated and then washed with a solution of sodium bicarbonate (3.5 g) in demineralised water (50 ml). The organic phase was separated and washed with citric acid (5.0 g) in demineralised water (50 ml), demineralised water (50 ml) and then concentrated in vacuo to an orange oil. The oil was taken up in acetonitrile (30 ml) and a solution of sodium bicarbonate (0.65 g, 4.1 mmol) in demineralised water (5 ml) was added. The solution was azeotropically dried by distillation at a constant volume of acetonitrile and the mixture was granulated at 20–25° C. overnight. The mixture was filtered and the residue dried in vacuo at 45° C. to give the title compound as a white solid (2.6 g, 43% yield, 95% pure by NMR).

$^1$H-NMR (CDCl$_3$) δ: 7.38–7.21 (5H, m), 7.10 (1 H, d, J 7.6 Hz), 7.05 (1 H, s), 7.02(1H, d J 7.2 Hz), 6.89 (1H, t, J 7.2 Hz), 3.30 (2H, s), 2.70–2.65 (2H, m), 2.47–2.41 (2H, m), 2.19 (3H, s), 1.40 (9H, s).

EXAMPLE 13

(R)-2-[2-(tert-butoxy)-2-oxoethyl]-5-(2-methyl-1,1'-biphenyl-4-yl)-pentanoic Acid

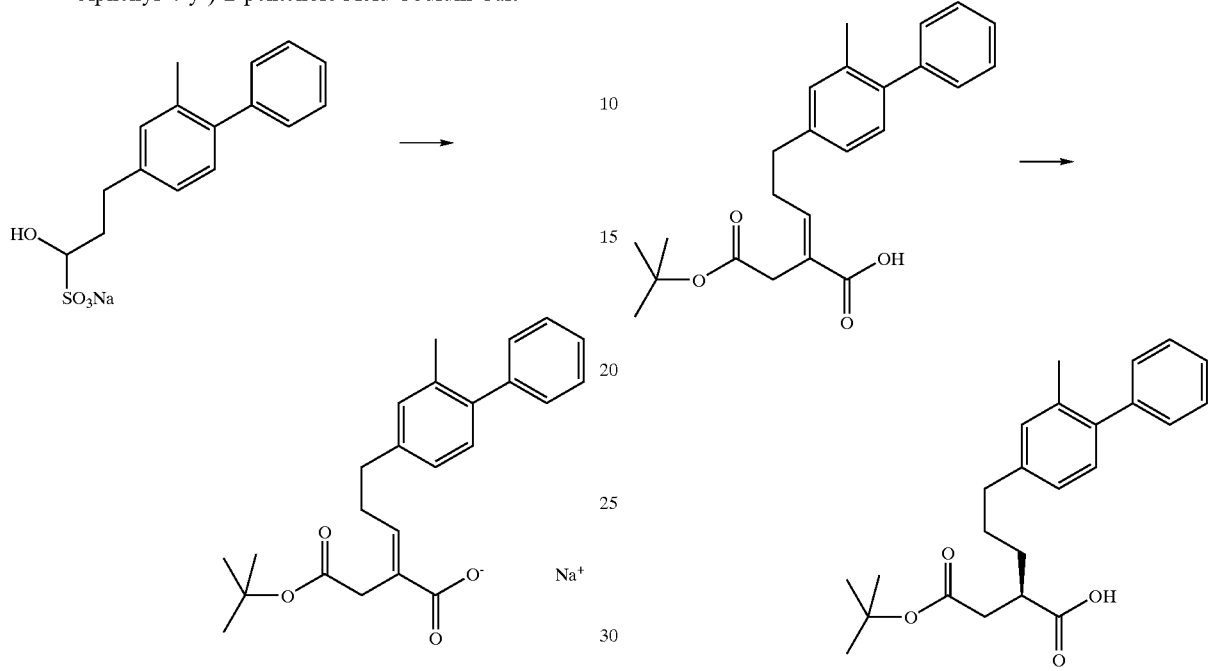

A solution of (E)-2-[2-(tert-butoxy)-2-oxoethyl]-5-(2-methyl-1,1'-biphenyl-4-yl)-2-pentenoic acid (3.8 g, 10 mmol) and 1,1'-bis[(2S,4S)-2,4-diethylphosphetano]ferrocene-(1,5-cyclooctadiene)-rhodium (I) tetrafluoroborate (7.8 mg, 10 μmol) in methanol (10 ml) was stirred at 20–25° C. for 24 hours, under hydrogen (60 p.s.i.). The mixture was then concentrated in vacuo to leave the title compound as a yellow oil (3.8 g, 98% conversion, enantiomeric excess=95%, 95% pure by NMR).

$^1$H-NMR (CDCl$_3$) δ: 7.42–7.30 (5H, m), 7.18–7.03 (3H, m), 2.94–2.82 (1H, m), 2.70–2.62 (3H, m), 2.41 (1 H, br dd), 2.23 (3H, s), 1.80–1.59 (4H, m), 1.43 (9H, s)

EXAMPLE 14

(R)-2-[2-(tert-butoxy)-2-oxoethyl]-5-(2-methyl-1,1'-biphenyl-4-yl)-pentanoic Acid Cyclohexylamine Salt

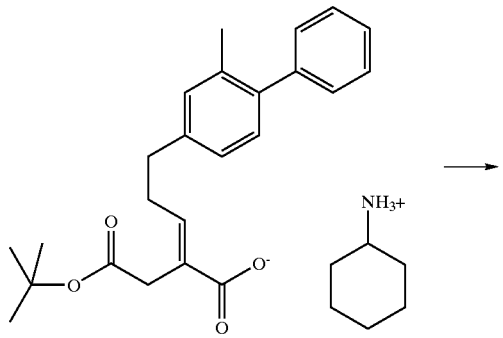

19
-continued

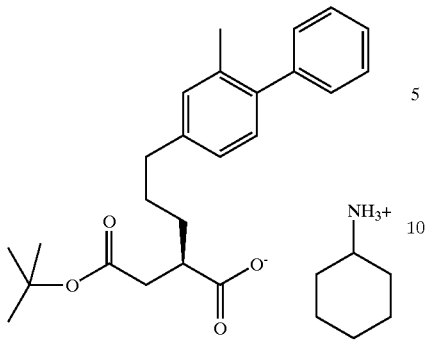

A stirred solution of (E)-2-[2-(tert-butoxy)-2-oxoethyl]-5-(2-methyl-1,1'-biphenyl-4-yl)-2-pentenoic acid cyclohexylamine salt (1.1 Kg, 2.3 mol) and [(S)-2,2'-bis(diphenylphosphino-1,1'-binaphthyl]chloro(p-cymene) ruthenium chloride (2.2 g, 2.4 mmol) in methanol (8.2 liters) and water (2.8 liters) was heated to 60° C., under hydrogen (60 p.s.i.), for 40 hours and then allowed to cool to 20–25° C. (enantiomeric excess=88%). The mixture was concentrated in vacuo to a volume of 3 liters and then ethyl acetate (5 liters) was added. The mixture was distilled at constant volume of ethyl acetate until water droplets appeared in the distillate. The mixture was then cooled to 20–25° C. and then demineralised water (2.9 liters) and citric acid (485 g, 2.5 mol) were added. The organic phase was separated and washed with demineralised water (1.1 liter) and then dried azeotropically by distillation at a constant volume of 8.25 liters. Methylethyl ketone (8.25 liters) was added and the mixture was warmed to 40° C. Cyclohexylamine (228 g, 2.28 mol) was added in one portion and the mixture was allowed to cool to 20–25° C., then was stirred for 16 hours. The mixture was filtered and the residue was washed with a mixture of ethyl acetate (55 ml) and methylethyl ketone (55 ml) and then dried in vacuo at 45° C. to leave the title compound as a colourless solid (0.71 Kg, 65% yield, enantiomeric excess=98.6%, 99% pure by HPLC).

$^1$H-NMR (CDCl$_3$) δ: 7.42–7.25 (5H, m), 7.11 (1 H, d, J 7.6 Hz), 7.08–7.00 (2H, m), 2.90–2.82 (1H, m), 2.67–2.58 (4H, m), 2.30 (1H, br dd), 2.23 (3H, s), 2.00–1.86 (2H, m), 1.80–1.50 (7H, m), 1.41 (9H, s), 1.38–1.09 (5H, m)

EXAMPLE 15

(R)-2-[2-(tert-butoxy)-2-oxoethyl]-5-(2-methyl-1,1'-biphenyl-4-yl)-pentanoic Acid (S)-alpha-methylbenzylamine Salt

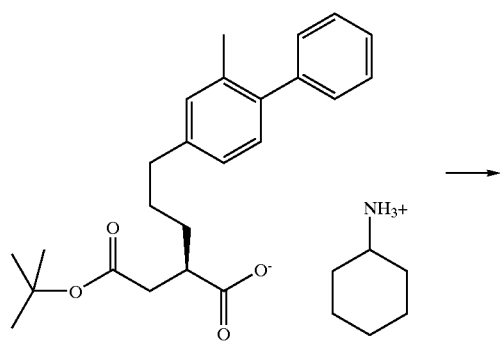

20
-continued

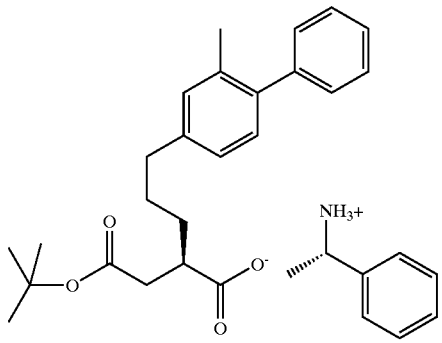

(R)-2-[2-(tert-butoxy)-2-oxoethyl]-5-(2-methyl-1,1'-biphenyl-4-yl)-pentanoic acid can be enantiomerically upgraded as the (S)-alpha-methylbenzylamine salt. Thus, (R)-2-[2-(tert-butoxy)-2-oxoethyl]-5-(2-methyl-1,1'-biphenyl-4-yl)-pentanoic acid cyclohexylamine salt (50 g, 0.10 mol, enantiomeric excess=72%) was partitioned between ethyl acetate (750 ml) and aqueous citric acid solution (10%, 750 ml). The organic phase was separated, washed with water (500 ml), then azeotropically dried by distillation at constant volume. (S)-alpha-methylbenzylamine (13.2 ml, 0.10 mol) was added dropwise over 5 min at 40° C., the mixture was allowed to cool to 20–25° C., and was then stirred for 24 hours. The mixture was filtered and the residue was washed with ethyl acetate (100 ml) and then dried in vacuo at 45° C. for 2 hours to leave the title compound as a colourless solid (41.0 g, 91% yield, enantiomeric excess=96.4%, 95% pure by NMR).

$^1$H-NMR (CDCl$_3$) δ: 7.40–7.22 (10H, m), 7.12 (1H, d, J 7.6 Hz), 7.06–7.02 (2H, m), 4.22–4.18 (1H, m), 2.80–2.76 (1H, m), 2.63–2.59 (3H, m), 2.34 (1H, dd, J 16.4, 5.6 Hz), 2.24 (3H, s), 1.77–1.70 (3H, m), 1.61–1.56 (1H, m), 1.47 (3H, d, J 6.8 Hz), 1.40 (9H, s)

What is claimed is:
1. A process for the preparation of a compound of the formula (IV)

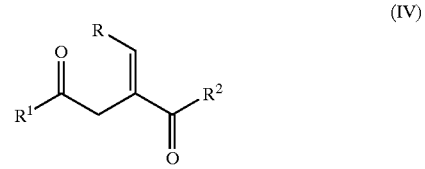

(IV)

wherein R is aryl, C$_{3-8}$ cycloalkyl, C$_{1-10}$ alkyl, (aryl)C$_{1-10}$ alkylene, (C$_{3-8}$ cycloalkyl)C$_{1-10}$ alkylene, heterocyclyl, (heterocyclyl)C$_{1-10}$ alkylene, (aryl)C$_{3-8}$ cycloalkylene, (C$_{3-8}$ cycloalkyl)arylene or (C$_{1-10}$ alkylaryl)C$_{1-10}$ alkylene, wherein aryl is a mono- or bicyclic partially or fully unsaturated carbocyclic ring system containing from 4 to 10 atoms, wherein aryl is a mono- or bicyclic partially or fully unsaturated carbocyclic ring system is phenyl or naphthyl, or a partially or fully unsaturated mono- or bicyclic heterocyclic moiety having up to 10 atoms in the ring system and with up to 4 hetero-atoms in the said ring system each independently selected from N, O and S, said carbocyclic ring system and heterocyclic moiety being optionally substituted by one or more substituents each independently selected from halogen, NO$_2$, NH$_2$, CO$_2$R$^6$, phenyl, C$_{1-6}$ alkyl (optionally substituted by one or more halogen), and $C_{1-6}$ alkoxy(optionally substituted by one or more halogen), and wherein heterocyclyl is a 3- to 8-membered mono or bicyclic saturated heterocyclic group having from 1 to 4 ring hetero-atoms each independently selected from N, O and S, optionally substituted by one or more substituents each independently selected from halogen, $NO_2$, $NH_2$, $CO_2R^9$, phenyl, $C_{1-6}$ alkyl(optionally substituted by one or more halogen), and $C_{1-6}$ alkoxy (optionally substituted by one or more halogen);

$R^1$ is $C_{1-6}$ alkoxy;

$R^2$ is OH or $O^-M^+$, wherein $M^+$ is a metal cation is sodium, lithium, or potassium;

$R^9$ is H or $C_{1-6}$ alkyl;

comprising reacting an aldehyde of formula RCHO, or a protected derivative thereof selected from the group consisting of a hemiacetal or adduct thereof wherein said adduct is a bisulphite, wherein R is as defined above, with a phosphorus compound of formula (IX):

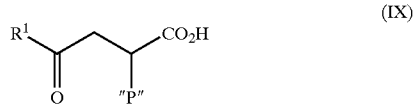

(IX)

or a metal carboxylate salt thereof, selected from the group consisting of a sodium, lithium or potassium carboxylate salt thereof, wherein $R^1$ is as defined above, and wherein P is a phosphonate moiety of formula —P(O)($OR^3$)($OR^4$), wherein $R^3$ and $R^4$ are each independently selected from H, $C_{1-6}$ alkyl, benzyl and phenyl (optionally substituted by one or more $C_{1-6}$ alkyl), or $R^3$ and $R^4$ taken together are $C_{2-5}$ alkylene, or P is a phosphorane moiety of formula —$(PR^5R^6R^7)^+X^-$ wherein $R^5$, $R^6$ and $R^7$ are each independently selected from $C_{1-6}$ alkyl and phenyl, and X is bromine, chlorine or iodine, in the presence of a sodium, lithium or potassium $C_1$–$C_6$ alkoxide base, in an inert solvent, and at a temperature of from –80° C. to 20° C.

2. The process according to claim, further comprising conversion of the product of formula (IV) when $R^2$ is $O^-M^+$ and wherein $M^+$ is a metal selected from the group consisting of Na, Li or K, to a compound of formula (IV) wherein $R^2$ is OH by treatment with a proton source.

3. The process according to claim 2, further comprising conversion of the compound of formula (IV) wherein $R^2$ is OH to a compound of formula (IV) wherein $R^2$ is $O^-M^+$, wherein $M^+$ is a protonated amine moiety by treatment with an amine.

4. The process according to claim 1, wherein the reaction time for the formation of the compound of formula IV is less than 24 hours.

5. The process according to claim 1 wherein R is (aryl) $C_{1-10}$ alkylene or ($C_{3-8}$ cycloalkyl)$C_{1-10}$ alkylene.

6. The process according to claim 5, where R is phenylethyl, cyclohexylethyl or (2-methyl-1,1'-biphenyl-4-yl)ethyl.

7. The process according to claim 1, wherein $R^1$ is t-butoxy.

8. A process according to claim 7, where $R^2$ is OH, $O^-Li^+$, $O^-Na^+$, $O^-K^+$, $O^-$cyclohexylammonium$^+$, $O^-$adamantanammonium$^+$, $O^-$triethanolammonium$^+$ or $O^-$(S)-α-methylbenzylammonium$^+$.

9. The process according to claim 8, wherein the reaction is carried out using the aldehyde RCHO or RCH(OH)$SO_3^-$ $Na^+$.

10. The process according to claim 1, wherein P is P(O)($OC_2H_5$)$_2$, P(O)($OCH_2CH_2O$) or a triphenylphosphinium halide moiety.

11. The process according to claim 10, where P is P(O)($OC_2H_5$)$_2$.

12. The process according to claim 1, where the base is potassium t-butoxide, sodium t-butoxide or sodium methoxide.

13. The process according to claim 1, wherein the reaction solvent is anhydrous tetrahydrofuran, anhydrous toluene or anhydrous $R^1H$, wherein $R^1$ is $C_{1-6}$ alkoxy, or a mixture thereof.

14. The process according to claim 13, where the reaction solvent is selected from tetrahydrofuran and toluene when the aldehyde RCHO is used as a substrate, and selected from tetrahydrofuran, t-butanol and toluene when the bisulphite adduct is used as a substrate.

15. The process according to claim 1, where the reaction is carried out at a temperature of from –20° C. to 10° C.

16. The process according to claim 15, where the reaction is carried out at a temperature of from –10° C. to 10° C.

17. The process according to claim 16, where the reaction is carried out at a temperature of from 0° C. to 5° C.

18. The process according to claim 1, where in the aldehyde RCHO is used as a substrate, and the reaction is carried out by adding the phosphorus compound to the base and solvent mixture, followed by addition of the aldehyde.

19. The process according to claim 1, where the aldehyde RCHO is used as substrate, and the reaction is carried out by combining the phosphorus compound and the aldehyde, followed by addition of the base.

20. The process according to claim 1, where the aldehyde RCHO is used as substrate, and the reaction is carried out by adding the base to the phosphorus compound followed by addition of the aldehyde.

21. The process according to claim 1, wherein bisulphite is used as the substrate, and the reaction is carried out by adding the base to a mixture of the bisulphite adduct and the phosphorus compound.

22. The process according to claim 1, wherein bisulphite is used as the substrate, and the reaction is carried out by adding the bisulphite to a mixture of the phosphorus compound and the base.

23. The process according to claim 3, wherein said protonated amine moiety is selected from the group consisting of mono($C_{1-10}$ alkyl)ammonium, di($C_{1-10}$ alkyl) ammonium, tri($C_{1-10}$ alkyl)ammonium, mono($C_{3-10}$cycloalkyl)ammonium, di($C_{3-10}$cycloalkyl)ammonium, tri ($C_{3-10}$cycloalkyl)ammonium, ($C_{1-10}$ alkyl)$_{n1}$ ($C_{3-10}$ cycloalkyl)$_{n2}$ammonium, anilinium, benzylammonium, triethanolammonium, and (S)-α-methylbenzylammonium, where n1 and n2 are each independently selected from 1 or 2 with the proviso that the sum of n1 and n2 is not greater than 3.

* * * * *